United States Patent [19]

Christiansen et al.

[11] Patent Number: 4,684,636

[45] Date of Patent: Aug. 4, 1987

[54] ANTIANDROGENIC SULFONYLSTEROIDOPYRAZOLES AND PROCESSES FOR PREPARATION METHOD OF USE AND COMPOSITIONS THEREOF

[75] Inventors: Robert G. Christiansen, Schodack; Malcolm R. Bell, East Greenbush; John L. Herrmann, Jr., Kinderhook; Chester J. Opalka, Jr., Schodack, all of N.Y.

[73] Assignee: Sterling Drug Inc., New York, N.Y.

[21] Appl. No.: 849,582

[22] Filed: Apr. 8, 1986

Related U.S. Application Data

[63] Continuation-in-part of Ser. No. 748,378, Jun. 24, 1985, abandoned.

[51] Int. Cl.$^4$ .................... A61K 31/58; C07J 21/00
[52] U.S. Cl. ............................ 514/176; 540/42
[58] Field of Search .................. 260/239.5; 514/176; 540/52

[56] References Cited

U.S. PATENT DOCUMENTS 3,704,295 11/1972 Clinton ........................ 260/239.5
4,297,350 10/1981 Bahcock et al. .............. 260/239.5

Primary Examiner—Leonard Schenkman
Assistant Examiner—Joseph A. Lipovsky
Attorney, Agent, or Firm—Theodore C. Miller; Dupont Paul E.

[57] ABSTRACT

1'-Sulfonylsteroido[3,2-c]pyrazoles, for example, (5α,1-7α)-1'-(methylsulfonyl)-1'H-pregn-20-yno[3,2-c]pyrazol-17-ol, which are useful as antiandrogenic agents, and processes for preparation, method of use and compositions thereof are disclosed.

19 Claims, No Drawings

ANTIANDROGENIC SULFONYLSTEROIDOPYRAZOLES AND PROCESSES FOR PREPARATION METHOD OF USE AND COMPOSITIONS THEREOF

CROSS-REFERENCE TO RELATED APPLICATION

This application is a continuation-in-part of our copending application Ser. No. 748,378 filed June 24, 1985, now abandoned.

BACKGROUND OF THE INVENTION

1. Field of the Invention

The invention relates to 1'-sulfonylsteroido[3,2-c]pyrazoles, which are useful as antiandrogenic agents, and processes for preparation, method of use and compositions thereof.

INFORMATION DISCLOSURE STATEMENT

Clinton U.S. Pat. No. 3,704,295 issued Nov. 28, 1972 describes steroido[3,2-c]pyrazoles having a substitutent designated R' on one or the other of the pyrazole nitrogen atoms wherein R' includes lower-alkyl radicals, e.g. methyl, ethyl, propyl, isopropyl, butyl, and the like; monocarbocyclic aryl radicals, e.g., phenyl, p-tolyl, and the like; lower-alkanoyl radicals, e.g., acetyl, propionyl, butyryl, and the like; monocarbocyclic aroyl radicals, e.g., benzoyl, p-nitrobenzoyl, p-toluyl, and the like; monocarbocyclic aryl-loweralkanoyl radicals, e.g., phenylacetyl, β-phenylpropionyl, p-chlorophenylacetyl, and the like; monocarbocyclic aryloxy-loweralkanoyl radicals, e.g. phenoxyacetyl, p-chlorophenoxy-acetyl, p-methoxyphenoxyacetyl, and the like; and the carbamyl and guanyl radicals. When compounds where R' represents acyl, carbamyl or guanyl radicals, the starting mono-substituted hydrazines are mono-acyl hydrazines, semicarbazide or aminoguanidine, respectively.

Alternatively, the compounds wherein R' represents hydrogen can be utilized as intermediates for preparing the compounds wherein R' represents an acyl radical or the carbamyl radical by reacting said compounds wherein R' represents hydrogen with the appropriate acid anhydride, or with cyanic acid (an alkali metal cyanate in the presence of mineral acid), respectively. The steroido[3,2-c]pyrazoles of the Clinton patent are described as possessing useful metabolic, hormonal or anti-hormonal properties. In particular they exhibit one or more of the following activities: anabolic, androgenic, pituitary inhibiting, estrogenic, progestational and adrenal cortical.

SUMMARY OF THE INVENTION

In a first composition of matter aspect the invention is a compound having the structural formula

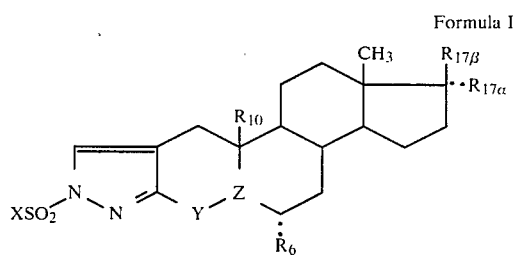

Formula I wherein
X is $CH_3$, $CH_3CH_2$, $CH_3CH_2CH_2$ or $ClCH_2$;
Y-Z is

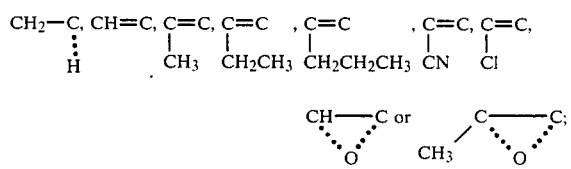

$R_6$ is H or $CH_3$ when Y-Z is CH=C or H when Y-Z is other than CH=C;
$R_{10}$ is H or $CH_3$;
$R_{17\alpha}$ taken alone is H, $CH_3$, $CH_2CH_3$, CH=$CH_2$, C≡CH or C≡CBr;
$R_{17\beta}$ taken alone is OH, $OCOCHCl_2$, $OCOCF_3$, $OCH_3$, $OCH_2SCH_3$, $OCH_2SOCH$, $OCH_2SO_2CH_3$ or

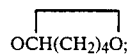

$OCH(CH_2)_4O$;

and
$R_{17\alpha}$ taken together with $R_{17\beta}$ is $OCH_2CH_2O$.

The compounds of Formula I are useful as antiandrogenic agents.

A preferred composition of matter aspect of the invention is a compound of Formula I wherein X is $CH_3$, Y-Z is

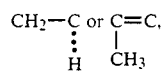

$R_6$ is H, $R_{10}$ is $CH_3$, $R_{17\alpha}$ is $CH_3$ or C≡CH and $R_{17\beta}$ is OH.

In a first process aspect the invention is the process of preparing a compound of Formula I which comprises sulfonylating the corresponding compound having the structural formula

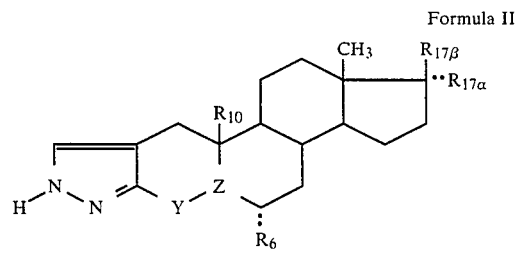

Formula II with the corresponding compound having the structural formula

XSO₂Q

Formula III wherein Q is Cl, Br or OSO₂X.

In a second process aspect the invention is the process of preparing a compound of Formula I which comprises condensing the corresponding compound having the structural formula

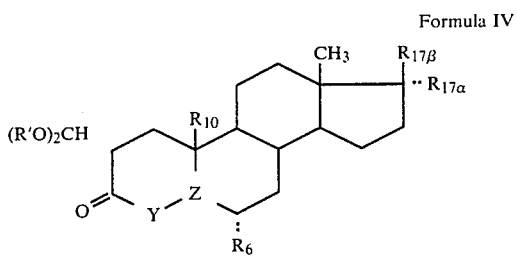

Formula IV with the corresponding compound having the structural formula

XSO₂NHNH₂

Formula V wherein R' is $CH_3$ or $CH_3CH_2$.

In a third process aspect the invention is the process of preparing a compound of Formula I which comprises condensing the corresponding compound having the structural formula

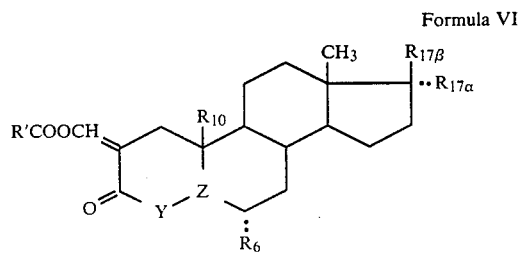

Formula VI with the corresponding compound having the structural formula

XSO₂NHNH₂

Formula V wherein R' is $CH_3CH_2$ or $C_6H_5$.

In a fourth process aspect the invention is the process for effecting an antiandrogenic response in a mammal which comprises administering to the mammal an antiandrogenically effective amount of a compound of Formula I.

In a second composition of matter aspect the invention is a composition which comprises an antiandrogenically effective concentration of a compound of Formula I and a pharmaceutically acceptable vehicle.

DETAILED DESCRIPTION OF THE INVENTION INCLUSIVE OF THE PREFERRED EMBODIMENTS

Preparation of the Compounds

In the preparative process aspects of the invention "corresponding" means that the variables of the reactants used to prepare a particular compound of Formula I are the same as those of the compound of Formula I.

The synthetic intermediates of Formulas II, III, IV, V and VI are known classes of compounds and are commercially available or can be made by methods specifically or generally described in the chemical literature.

The compounds of Formula II are steroido[3,2-c]pyrazoles and are described by, or can be made by the methods described in, above-cited Clinton U.S. Pat. No. 3,704,295.

The compounds of Formula III wherein Q is Cl, which are sulfonyl chlorides, are commercially available. The compounds of Formula III wherein Q is OSO₂X are sulfonic acid anhydrides and are commercially available or can be made from the corresponding sulfonic acids by warming with phosphorous pentoxide. The compounds of Formula III wherein Q is Br, which are sulfonyl bromides, can be made from the corresponding sulfonic anhydrides by heating with hydrogen bromide at 105° C.

The compounds of Formula IV, which are 2α-dimethoxymethyl or diethoxymethyl-3-keto steroids, are made by dimethoxymethylating or diethoxymethylating the corresponding 3-keto steroids with the reagent made from trimethyl orthoformate or triethyl orthoformate (the latter is preferred) and boron trifluoride etherate (dimethoxycarbenium or diethoxycarbenium fluoborate) at low temperature by the method of Mock et al. (William L. Mock and Huei-Ru Tsou, J. Org. Chem., 1981, vol. 46, pp. 2557-2561).

The compounds of Formula V, which are sulfonyl hydrazides, are commercially available or can be made from the corresponding sulfonyl chlorides and hydrazine hydrate in ethanol.

The compounds of Formula VI are 2-acetoxymethylene, propionoxymethylene or benzoyloxymethylene-3-keto steroids and are made from the corresponding known 2-hydroxymethylene-3-keto steroids and acetic anhydride or propionic anhydride or a mixed anhydride thereof, for example, the mixed anhydride made from the acid and methanesulfonyl chloride, or benzoyl chloride, respectively.

The first process aspect of the invention is carried out at a temperature in the range of 0°-100° C. in an inert solvent and in the presence of an acid acceptor for the hydrogen chloride, hydrogen bromide or sulfonic acid produced as a by-product of the reaction. The acid acceptor is preferably a tertiary amine. The inert solvent and the acid acceptor can be the same substance, for example, pyridine, which is the preferred inert solvent and acid acceptor. Sulfonylation occurs predominantly at the 1'-position of the pyrazole ring but can also occur to the extent of up to about 30% at the 2'-position of the pyrazole ring. Separation of the desired 1'-isomer from the 2'-isomer may therefore be necessary, for example, by fractional crystallization, column chromatography or high pressure liquid chromatography (HPLC). The extent of 2'-sulfonylation is generally less when the 4-position of the steroid nucleus is substituted.

The second process aspect of the invention, which produces the 1'-isomer of Formula I selectively, is carried out at a temperature in the range of 0°-100° C. in an inert solvent. Tetrahydrofuran is the preferred inert solvent.

The third process aspect of the invention, which also produces the 1'-isomer of Formula I selectively, is carried out at a temperature in the range of 0°-100° C. in an inert solvent. Acetic acid or a mixture of acetic acid and dichloromethane is the preferred solvent.

Some compounds of Formula I can also be prepared from other compounds of Formula I or from closely related compounds. A compound of Formula I wherein $R_{17\alpha}$ is $CH=CH_2$ can be made from the corresponding compound wherein R is $C\equiv CH$ by catalytic hydrogenation using, for example, palladium on strontium carbonate as catalyst and pyridine as solvent. A compound of Formula I wherein $R_{17\alpha}$ is $CH_2CH_3$ can be made from the corresponding compound of Formula I wherein $R_{17\alpha}$ is $CH=CH_2$ or $C\equiv CH$ by catalytic hydrogenation using, for example, palladium on carbon as catalyst and ethanol as solvent. A compound of Formula I wherein $R_{17\alpha}$ is $C\equiv CBr$ can be made from the corresponding compound of Formula I wherein $R_{17\alpha}$ is $C\equiv CH$ by bromination using, for example, N-bromosuccinimide. A compound of Formula I wherein Y-Z is

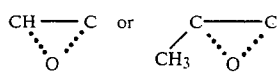

can be made from the corresponding compound of Formula I wherein Y-Z is $CH=C$ or

respectively, by epoxidation with a peracid, for example, m-chloroperbenzoic acid. A compound of Formula I wherein $R_{17\alpha}$ is H and $R_{17\beta}$ is OH can be made from the corresponding 17-keto compound by reduction with a metal hydride, for example, sodium borohydride. A compound of Formula I wherein $R_{17\alpha}$ is H and $R_{17\beta}$ is $OCOCHCl_2$ can be made from the corresponding compound of Formula I wherein $R_{17\alpha}$ is H and $R_{17\beta}$ is OH by dichloroacetylation using, for example, dichloroacetic anhydride. A compound of Formula I wherein $R_{17\beta}$ is $OCH_2SOCH_3$ or $OCH_2SO_2CH_3$ can be made from the corresponding compound of Formula I wherein $R_{17\beta}$ is $OCH_2SCH_3$ by S-oxidation using a peracid, for example, m-chloroperbenzoic acid.

In the examples set forth below structures of products are inferred from structures of starting materials and expected courses of preparative reactions. Structural confirmation and estimation of purity of starting materials and products are measured by melting temperature range (m.r.), elemental analysis, infrared (IR) spectral analysis, ultraviolet (UV) spectral analysis, nuclear magnetic resonance (NMR) spectral analysis, gas chromatography (GC), high pressure liquid chromatography (HPLC) and thin layer chromatgraphy (TLC).

EXAMPLE 1

A. Methanesulfonyl chloride (5.09 ml., 7.53 g., 0.0658 mole) was added with stirring and cooling at ice bath temperature to a solution of $(5\alpha,17\alpha)$-1'H-pregn-20-yno[3,2-c]pyrazol-17-ol (14.60 g., 0.432 mole) in pyridine (75 ml.). The temperature of the mixture rose to about 20° C. after the addition, then returned to 0°–5° C. TLC showed that the reaction was complete after 1 hr. Water (125 ml.) was then added with continued stirring and cooling. An oil separated and crystallized. The crystals were collected, washed and dried (15.50 g.). The remaining product (11 g.) was isolated by extraction of the mother liquor with dichloromethane.

The reaction was repeated using 18.36 g. (0.0542 mole) of $(5\alpha,17\alpha)$-1'H-pregn-20-yno[3,2-c]pyrazol-17-ol and 9.31 g. (0.0813 mole) of methanesulfonyl chloride. The product was isolated entirely by dichloromethane extraction.

The combined products of both reactions, TLC of which showed a larger faster running spot and a smaller slower running spot, were purified by column chromatography on silica gel (Whatmans LPS2, 500 g.). Elution was begun with dichloromethane-ether (99:1). Fractions of 400 ml. were collected. The solid residues of fractions 6–14 (23.25 g.), TLC of which showed only the faster running spot, were combined and recrystallized from acetonitrile, affording $(5\alpha,17\alpha)$-1'-(methylsulfonyl)-1'H-pregn-20-yno[3,2-c]pyrazol-7-ol (18.59 g., 46% yield, m.r. 200°–202° C.), the compound of Formula I wherein X and $R_{10}$ are $CH_3$, Y-Z is

$R_6$ is H, $R_{17\alpha}$ is $C\equiv CH$ and $R_{17\beta}$ is OH.

B. A mixture of $(5\alpha,17\alpha)$-1'-(methylsulfonyl)-17-[(methylthio)methoxy]-1'H-pregn-20-yno[3,2-c]pyrazole (product of part C of Example 26, 19.00 g., 0.0400 mole), methyl iodide (10 ml., 0.16 mole), sodium bicarbonate (8.4 g., 0.10 mole), water 0.72 ml., 0.040 mole) and acetone (500 ml.) was stirred under reflux for 20 hr. More methyl iodide (10 ml.) was added and stirring and refluxing were continued for 24 hr. The mixture was filtered and the filtrate was stripped of volatiles. The residue was partitioned between dichloromethane (300 ml.) and dilute aqueous sodium thiosulfate solution (300 ml.). The dichloromethane layer was separated and the aqueous layer was extracted again with dichloromethane (50 ml.). The combined dichloromethane extracts were dried and stripped of solvent. A solution of the residue in dichloromethane (90 ml.) and ether (10 ml.) was passed through silica gel (50 g.) using more dichloromethane-ether (9:1). The residue (15.5 g.) from the first fraction (300 ml.) was recrystallized twice from acetonitrile, affording $(5\alpha,17\alpha$-1'-(methylsulfonyl)-1'H-pregn-20-yno[3,2-c]pyrazol-17-ol (12.31 g., 74% yield, m.r. 196°–197° C.).

C. A solution of $(5\alpha,17\alpha)$-1'-(methylsulfonyl)-1'H-pregn-20-yno[3,2-c]pyrazol-17-ol trifluoroacetate (ester) (product of part C of Example 28 and the entire product of the condensation of $(2\alpha,5\alpha,17\alpha)$-2-(diethoxymethyl)-17-[(trifluoroacetyl)oxy]pregn-20-yn-3-one (10.25 g., 0.0200 mole) and methanesulfonylhydrazide (2.42 g., 0.0220 mole) by the method of part B of Example 20) in 100 ml. of a solution prepared from chloroform (210 ml.), ethanol (100 ml.) and concentrated aqueous ammonia (10 ml.) was allowed to stand at room temperature for 2 hr., diluted with chloroform (250 ml.), and washed with dilute hydrochloric acid (2N, 250 ml.). The chloroform layer was dried and stripped of chloroform under vacuum. A solution of the residue in dichloromethane (95 ml.) and ether (5 ml.) was passed through silica gel (50 g.) using more dichloromethane-ether (19:1, 600 ml.). Evaporation of the solvent and recrystallization of the residue from acetonitrile afforded (5α,17α)-1'-(methylsulfonyl)-1'H-pregn-20-yno[3,2-c]pyrazol-17-ol (7.07 g., 85% yield, m.r. 202°–203° C.).

D. (a) Methanesulfonyl chloride (196 ml., 290 g., 2.50 mole) was added over 1 hr. with stirring at room temperature to a mixture of (5α,17α)-17-hydroxy-2-(hydroxymethylene)pregn-20-yn-3-one (295.2 g., 0.86 mole), sodium acetate (244 g., 2.9 mole) and glacial acetic acid (1.6 l.) and stirring was continued overnight. The mixture was filtered and acetic acid (1. l.) was distilled from the filtrate under vacuum. The residual mixture was poured slowly into ice-water (8 l.) with vigorous stirring. The resulting solid was collected by filtration, washed twice with water (600 ml. each time), dried (292.4 g.), slurried with methyl t-butyl ether (500 ml.), collected by filtration again, washed with hexane-methyl t-butyl ether (1:1, 100 ml.) and dried, affording (5α,17α)-2-(acetoxymethylene)-17-hydroxypregn-20-yn-3-one (197.8 g., 60% yield, m.r. 122°–129° C.).

(b) A solution of methanesulfonylhydrazide (82.5 g., 0.75 mole) in acetic acid (100 ml.) was added with stirring over 5 min. to a mixture of (5α,17α)-2-(acetoxymethylene)-17-hydroxypregn-20-yn-3-one (197 g., 0.51 mole) and acetic acid (1 l.). The mixture was stirred for 1 hr. at room temperature, forming a deep yellow solution, which was poured with vigorous stirring into ice-water (6 l.). The resulting solid was collected by filtration, washed twice with water (500 ml. each time), pressed dry, washed twice again with water (500 ml. each time), dried (245 g.), recrystallized, first from acetonitrile (2.5 volumes) and then from methanol (6.6 volumes), dried, ground, and redried, affording (5α,17α)-1'-(methylsulfonyl)-1'-H-pregn-20-yno[3,2-c]pyrazol-17-ol (137.8 g., 65% yield, m.r. 194°–196° C.).

EXAMPLE 2

By the method of part A of Example 1 (17β)-1'H-17-methylandrost-4-eno[3,2-c]pyrazol-17-ol (32.6 g., 0.100 mole) was methanesulfonylated using methanesulfonyl chloride (17.18 g., 11.6 ml., 0.149 mole) in pyridine (150 ml.). The product was purified by HPLC on silica gel using dichloromethane-ether (9:1) as eluant followed by crystallization from ether and recrystallization from acetonitrile, affording (17β)-17-methyl-1'-(methanesulfonyl)-1'H-androst-4-eno[3,2-c]-pyrazol-17-ol (22.51 g., 56% yield, m.r. 203°–205° C.), the compound of Formula I wherein X, $R_{10}$ and $R_{17\alpha}$ are $CH_3$, Y-Z is CH=C, $R_6$ is H and $R_{17\beta}$ is OH.

EXAMPLE 3

By the method of part A of Example 1 (17α)-1'H-pregn-4-en-20-yno[3,2-c]pyrazol-17-ol (33.7 g., 0.100 mole) was methanesulfonylated using methanesulfonyl chloride (17.18 g., 11.6 ml., 0.149 mole) in pyridine (150 ml.). The product was purified by column chromatography on silica gel (E. Merck Kieselgel 60, 400 g.). The solid residues of fractions (400 ml. each) 6–16 of the dichloromethane-ether (99:1) eluate were combined (14.11 g.) and recrystallized from methanol (50 ml.)-water (5 ml.), affording (17α)-1'-(methanesulfonyl)-1'H-pregn-4-en-20-yno[3,2-c]pyrazol-17-ol (12.82 g., 32% yield, m.r. 205°–207° C.), the compound of Formula I wherein X and $R_{10}$ are $CH_3$, Y-Z is CH=C, $R_6$ is H, $R_{17\alpha}$ is C≡CH and $R_{17\beta}$ is OH.

EXAMPLE 4

By the method of part A of Example 1 (5α,17β)-1'H-17-methylandrostano[3,2-c]pyrazol-17-ol (37.00 g., 0.113 5 mole) was methanesulfonylated using methanesulfonyl chloride (11.95 ml., 17.55 g., 0.15 mole) in pyridine (150 ml.). The crystalline product (44.07 g.) was purified by HPLC on silica gel using dichloromethane-ether (9:1) as eluant followed by recrystallization from methanol, affording (5α,17β)-17-methyl-1'-(methylsulfonyl)-1'H-androstano[3,2-c]-pyrazol-17-ol (25.47 g., 55% yield, m.r. 189°–190° C.), the compound of Formula I wherein X, $R_{10}$ and $R_{17\alpha}$ are methyl, Y-Z is

$R_6$ is H and $R_{17\beta}$ is OH.

EXAMPLE 5

By the method of part A of Example 1 (17α-1'H-pregn-20-yno[3,2-c]pyrazol-17-ol (16.30 g., 0.0482 mole) was ethanesulfonylated using ethanesulfonyl chloride (9.17 g., 0.071 mole) in pyridine (150 ml.). The crystalline product (16.75 g.) was purified by HPLC on silica gel using dichloromethane-ether (9:1) as eluant followed by recrystallization from methanol, affording (5α,17α)-1'-(ethylsulfonyl)-1'H-pregn-20-yno[3,2-c]pyrazol-17-ol (12.11 g., 58% yield, m.r. 191°–193° C.), the compound of Formula I wherein X is $CH_3CH_2$,

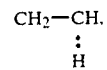

$R_6$ is H, $R_{10}$ is $CH_3$, $R_{17\alpha}$ is C≡CH and $R_{17\beta}$ is OH.

EXAMPLE 6

By the method of part A of Example 1 (17α)-1'H-pregn-20-yno[3,2-c]pyrazol-17-ol (16.10 g., 0.0476 mole) was propanesulfonylated using propanesulfonyl chloride (10.12 g., 0.071 mole) in pyridine (150 ml.). The crystalline product (23.54 g.) was purified by HPLC on silica gel using dichloromethane-ether (19:1) as eluant followed by recrystalization from methanol, affording (5α,17α)-1'-(propylsulfonyl)-1'H-pregn-20-yno[3,2-c]pyrazol-17-ol (10.97 g., 52% yield, m.r. 182°–183° C.), the compound of Formula I wherein X is $CH_3CH_2CH_2$, Y-Z is

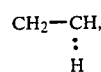

$R_6$ is H, $R_{10}$ is $CH_3$, $R_{17\alpha}$ is C≡CH and $R_{17\beta}$ is OH.

EXAMPLE 7

A mixture of a solution of (5α, 17α)-1'-(methylsulfonyl)-1'H-pregn-20-yno[3,2-c]pyrazol-17-ol (product of Example 1, 19.4 g., 0.0466 mole) in pyridine (300 ml.) and palladium on strontium carbonate catalyst (2%, 1.9 g.) was hydrogenated with mechanical shaking at room temperature for 6.5 hr. under pressure beginning at 40 p.s.i., allowed to stand overnight without hydrogen and filtered through infusorial earth. The filter bed was washed with ethyl acetate and the filtrate was stripped of volatiles under vacuum. Since TLC showed that the residue contained unchanged starting material, it was rehydrogenated by the same procedure. A solution of the product in dichloromethane was decolorized with charcoal and stripped of solvent. The residue was crystallized from ethanol in two crops, affording (5α,17α)-1'-(methylsulfonyl)-1'H-pregn-20-eno[3,2-c]-pyrazol-17-ol (11.2 g., m.r. 171.5°–173° C.; 3 g.; 73% yield), the compound of Formula I wherein X and $R_{10}$ are $CH_3$, X-Y is

$R_6$ is H, $R_{17\alpha}$ is $CH=CH_2$ and $R_{17\beta}$ is OH.

EXAMPLE 8

By the method of part A of Example 1 (5α,17α)-1'H-19-norpregn-20-yno[3,2-c]pyrazol-17-ol (20 g., 0.062 mole) was methanesulfonylated using methanesulfonyl chloride (10 ml.) in pyridine (400 ml.). The product was purified by HPLC on silica gel using hexane-ether (1:1) as eluant. The procedure was repeated using the same amounts of materials and the same method of purification. The products were combined and crystallized from ethyl acetate-hexane, affording (5α,17α)-1'-(methylsulfonyl)-1'H-19-norpregn-20-yno[3,2-c]-pyrazol-17-ol (8.2 g., 17% yield, m.r. 176°–178° C.), the compound of Formula I wherein X is $CH_3$, X-Y is

$R_6$ and $R_{10}$ are H, $R_{17\alpha}$ is C≡CH and $R_{17\beta}$ is OH.

EXAMPLE 9

A mixture of a solution of (5α,17α)-1'-(methylsulfonyl)-1'H-pregn-20-yno[3,2-c]pyrazol-17-ol (product of Example 1, 13 g., 0.0312 mole) and (5α, 17α)-1'-(methylsulfonyl)-1'H-pregn-20-eno[3,2-c]pyrazol-17-ol (product of Example 7, 3 g., 0.0072 mole) in ethanol (300 ml.) and palladium on carbon catalyst (10%, 1.6 g.) was hydrogenated with mechanical shaking at room temperature under pressure beginning at 40 p.s.i. After 3.3 hr. the hydrogenation was shown to be incomplete by TLC and was therefore continued for 4 hr. more beginning at 40 p.s.i. again. The mixture was filtered through infusorial earth. The filter bed was washed with ethyl acetate and the filtrate was stripped of volatiles under vacuum. Crystallization of the residue from ethanol afforded (5α,17α)-1'-(methylsulfonyl)-1'H-pregnano[3,2-c]pyrazol-17-ol (10.1 g., 63% yield, m.r. 194.5°–195.5° C.), the compound of Formula I wherein X and $R_{10}$ are $CH_3$, Y-Z is

$R_6$ is H, $R_{17\alpha}$ is $CH_2CH_3$ and $R_{17\beta}$ is OH.

EXAMPLE 10

By the method of part A of Example 1 (17β)-4,17-dimethyl-1'H-androst-4-eno[3,2-c]pyrazol-17-ol (34.0 g., 0.10 mole) was methanesulfonylated using methanesulfonyl chloride (17.19 g., 11.6 ml., 0.15 mole) in pyridine (150 ml.). The reaction time was 1.5 hr. 3-(Dimethyl)propylamine (10 ml.) was added to the reaction mixture, which was then quenched in dilute hydrochloric acid (2N, 1200 ml.) containing ice. The resulting solid was collected, washed with water, dried (41.30 g.) and recrystallized from ethanol, affording (17β)-4,17-dimethyl-1'-(methylsulfonyl)-1'H-androst-4-eno[3,2-c]-pyrazol-17-ol (30.13 g., 72% yield, m.r. 219°–220° C.), the compound of Formula I wherein X, $R_{10}$ and $R_{17\alpha}$ are $CH_3$, Y-Z

$R_6$ is H and $R_{17\beta}$ is OH.

EXAMPLE 11 m-Chloroperbenzoic acid (80% pure, 7.11 g., 0.033 mole) was added to a solution of (17β)-4,17-dimethyl-1'-(methylsulfonyl)-1'H-androst-4-eno[3,2-c]pyrazol-17-ol (product of Example 10, 12.56, 0.0300 mole) in dichloromethane (200 ml.). The mixture was allowed to stand for four days at room temperature, then filtered. The filtrate was washed with aqueous sodium sulfite solution and saturated aqueous sodium bicarbonate solution, dried and stripped of solvent. Recrystallization of the resulting solid (13.07 g., m.r. 186°–187° C.) from dichloromethane-methanol afforded (4α,5α,17β)-4,5-epoxy-4,17-dimethyl-1'-(methylsulfonyl)-1'H-androstano[3,2-c]pyrazol-17-ol (11.33 g., 87% yield, m.r. 199°–200° C.), the compound of Formula I wherein X, $R_{10}$ and $R_{17\alpha}$ are $CH_3$, Y-Z is

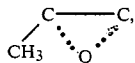

$R_6$ is H and $R_{17\beta}$ is OH.

EXAMPLE 12

By the method of part A of Example 1 in two runs (5α,17β)-1'H-androstano[3,2-c]pyrazol-17-ol (3.60 g., 0.0100 mole; 32.73 g., 0.0907 mole) was methanesulfonylated using methanesulfonyl chloride (1.26 g., 0.85 ml., 0.011 mole; 7.51 ml., 10.90 g., 0.0932 mole) in pyridine (25 ml., 125 ml.). The combined products were purified by column chromatography on silica gel (Whatmans LPS2, 1 kg.) using dichloromethaneether (99:1) as eluant. Fractions of 800 ml. were taken. Recrystallization of the combined residue (17.30 g.) of fractions 16–23 from dichloromethane (50 ml.) - methanol (300 ml.) (final volume 150 ml.) afforded (5α,17β)-1'-(methylsulfonyl)-1'H-androstano[3,2-c]pyrazol-17-ol hydrate (4:1) (13.42 g., 33% yield, m.r. 176°–178° C.), the compound of Formula I wherein X and $R_{10}$ are $CH_3$, Y-Z is

$R_6$ and $R_{17\alpha}$ is OH.

EXAMPLE 13

A. In two runs a mixture of 4-methyl-1'-(methylsulfonyl)-1'H-androst-4-eno[3,2-c]pyrazol-17-one cyclic 17-(1,2-ethanediyl acetal) (product of Example 14; 2.0 g., 0.0045 mole; 62.2 g., 0.14 mole) and acetic acid (80%, 12.5 ml., 40 ml.) was heated on a steam bath. The crude products were collected by filtration in two crops, combined and recrystallized from ethyl acetate, affording 4-methyl-1'-(methylsulfonyl)-1'H-androst-4-eno[3,2-c]pyrazol-17-one (43.45 g., 75% yield, m.r. 240.5°-242.5° C.).

B. A solution of sodium borohydride (1.19 g., 0.050 mole) in water (9 ml.) was added to a solution of 4-methyl-1'-(methylsulfonyl)-1'H-androst-4-eno[3,2-c]pyrazol-17-one (20.1 g., 0.0500 mole) in tetrahydrofuran (650 ml.) and the mixture was stirred at room temperature for 1.5 hr. Acetone (200 ml.) was added and the mixture was stirred for 0.5 hr. and stripped of volatiles. Dichloromethane was added and the mixture was filtered. The residue (20.7 g.) from evaporation of the filtrate was crystallized from acetonitrile (18.4 g., m.r. 154°-165° C.), combined with product (0.68 g., m.r. 154°-164° C.) from an earlier small scale (0.003 mole of steroid) run, and recrystallized from acetonitrile, affording (17β)-4-methyl-1'-(methylsulfonyl)-1'H-androst-4-eno[3,2-c]pyrazol-17-ol (16.4 g., 77% yield, m.r. 158°-166° C. with resolidification and remelting at 199°-201° C.), the compound of Formula I wherein X and $R_{10}$ are methyl, Y-Z is

$R_6$ and $R_{7\alpha}$ are H and $R_{17\beta}$ is OH.

EXAMPLE 14

By the method of part A of Example 1 4-methyl-1'H-androst-4-eno[3,2-c]pyrazol-17-one cyclic 17-(1,2-ethanediyl acetal) (12.0 g., 0.0326 mole) was methanesulfonylated using methanesulfonyl chloride (4 ml., 0.052 mole) in pyridine (100 ml.). The product was recrystallized twice from acetonitrile, affording 4-methyl-1'-(methylsulfonyl)-1'H-androst4-eno[3,2-c]pyrazol-17-one cyclic 17-(1,2-ethanediyl acetal) (10.7 g., 73% yield, m.r. 234°-237° C.), the compound of Formula I wherein X and $R_{10}$ are $CH_3$, Y-Z is

$R_6$ is H and $R_{17\alpha}$ and $R_{17\beta}$ taken together are $OCH_2CH_2O$.

EXAMPLE 15

By the method of part A of Example 1 (17β)-1'H-androst-4-eno[3,2-c]pyrazol-17-ol (36.02 g., 0.115 mole) was methanesulfonylated using methanesulfonyl chloride (13.83 g., 9.35 mol., 0.120 mole) in pyridine (250 ml.). The product was purified by HPLC on silica gel (17.02 g.) followed by recrystallization from chloroform (200 ml.) ethanol (200 ml.) (final volume 300 ml.), affording (17β)-1'-(methylsulfonyl)-1'H-androst-4-eno[3,2-c],pyrazol-17-ol (13.83 g., 31% yield, m.r. 227°-229° C.), the compound of Formula I wherein X and $R_{10}$ are $CH_3$, Y-Z is CH=C, $R_6$ and $R_{17\alpha}$ are H and $R_{17\beta}$ is OH.

EXAMPLE 16

Ethereal ethyl magnesium bromide (3.1 molar, 55 ml., 0.17 mole) was added to tetrahydrofuran (250 ml.) during 1.7 hr. while acetylene was bubbled through the solution. The resulting mixture was cooled in an ice bath and a solution of 4-methyl-1'-(methylsulfonyl)-1'H-androst-4-eno[3,2-c]pyrazol-17-one product of part A of Example 13, (32.4 g., 0.0804 mole) in tetrahydrofuran (380 ml.) was added. The ice bath was removed and the resulting mixture was stirred at room temperature for 3.3 hr., then quenched in saturated aqueous ammonium chloride solution (1.2 l.). The layers were separated. The aqueous layer was extracted with dichloromethane. The combined organic layers were washed with saturated aqueous sodium chloride solution and stripped of volatiles. A solution of the residual yellow gum (36 g.) was chromatographed on a column of silica gel (500 g.). Fractions of 400 ml. were taken. The eluant of fractions 1-2 was dichloromethane-hexane (3:1), of fractions 3-7 dichloromethane-hexane (7:1), of fractions 8-18 dichloromethane, of fractions 19-22 dichloromethane-ether (19:1). The residue of fractions 11-21 (14.9 g.) was combined with the corresponding residue of a 0.0497 mole run (6.35 g.) and recrystallized three times from toluene, affording (17α)-4-methyl-1'(methylsulfonyl)-1'H-pregn-4-en-20-yno-[3,2-c]pyrazol-17-ol (12.45 g., 22% yield, m.r. 221°-224° C.), the compound of Formula I wherein X and $R_{10}$ are $CH_3$, Y-Z is

$R_6$ is H, $R_{17\alpha}$ (is C≡CH and R)$_{17\beta}$ is OH.

EXAMPLE 17

By the method of Example 7 in two runs (17α)-4-methyl-1'-(methylsulfonyl)-1'H-pregn-4-en-20-yno[3,2-c]-pyrazol-17-ol (product of Example 16; about 3.7 g., about 0.0086 mole; 2.25 g., 0.00525 mole) was hydrogenated over palladium on strontium carbonate catalyst in pyridine. The combined products were crystallized and recrystallized from acetonitrile, affording (17α)-4-methyl-1'H-(methylsulfonyl)-1'H-pregna-4,20-dieno[3,2-c]pyrazol-17-ol (2.5 g., 42% yield, m.r. 195°-196° C.), the compound of Formula I wherein X and $R_{10}$ are $CH_3$, Y-Z is

$R_6$ is H, $R_{17\alpha}$ is CH=$CH_2$ and $R_{17\beta}$ is OH.

EXAMPLE 18

In two runs chloromethylsulfonyl chloride (1.7 ml., 0.019 mole; 4 ml., 0.044 mole) was added to a solution of (5α,17α)-1′H-pregn-20-yno[3,2-c]pyrazol-17-ol (3.38 g., 0.0100 mole; 8.5 g., 0.025 mole) in pyridine (20 ml., 35 ml.). The resulting solution was allowed to stand at room temperature for 1–3 hr., then poured into water (300 ml., 350 ml.). The gumming products were purified by a combination of crystallization from cyclohexane or tetrachloromethane and column chromatography on silica gel using dichloromethane as eluant and combined, affording (5α,17α)-1′-[(chloromethyl)sulfonyl]-1′H-pregn-20-yno[3,2-c]pyrazol-17-ol (5.4 g., 34% yield, m.r. 168°–170° C.), the compound of Formula I wherein X is ClCH$_2$, Y-Z is

R$_6$ is H, R$_{10}$ is CH$_3$, R$_{17\alpha}$ (is C≡CH and R)$_{17\beta}$ is OH.

EXAMPLE 19

By the method of part A of Example 1 in two runs (6α,17β)-6-methyl-1′H-androst-4-eno[3,2-c]pyrazol-17-ol (about 0.01 mole and about 0.05 mole) was methanesulfonylated using methanesulfonyl chloride (0.5 ml., 6 ml.) in pyridine (35 ml., 150 ml.). The products (3.5 g., 18 g.) were combined and purified by column chromatography on silica gel (400 g., elution with 19:1 dichloromethane-ethyl acetate) followed by recrystallization from acetonitrile, affording (6α,17β)-6-methyl-1′-(methylsulfonyl)-1′H-androst-4-eno[3,2-c]pyrazol-17-ol (2.4 g., 10% yield, m.r. 183°–188° C.), the compound of Formula I wherein X, R$_6$ and R$_{10}$ are CH$_3$, Y-Z is CH=C, R$_{17\alpha}$ is H and R$_{17\beta}$ is OH.

EXAMPLE 20

A. Under an argon atmosphere at less than −30° C. boron trifluoride etherate (100 ml., 115.4 g., 0.704 mole) was added to a solution of triethylorthoformate (109.5 ml., 97.56 g., 0.658 mole) in dichloromethane (300 ml.). The temperature was raised to 0° C., kept there for 15 min., then lowered to −70° C. A solution of (5α,17β)-17-[(tetrahydro-2H-pyran-2-yl)oxy]androstan-3-one (0.3 mole) in dichloromethane (250 ml.+50 ml. for rinsing) was then added, followed by diisopropylethylamine (166.5 ml., 123.5 g., 0.955 mole), the latter while maintaining the temperature at less then −55° C. The temperature was lowered to −70° C. for 1 hr. The mixture was then quenched in aqueous sodium bicarbonate solution (3 l., made by dissolving 300 g. of sodium bicarbonate in 3.5 l. of water). The layers were separated. The aqueous layer was extracted with dichloromethane (250 ml.). The combined dichloromethane layers were washed twice with cold hydrochloric acid (2N, 1200 ml., 600 ml.), then with half-saturated aqueous sodium bicarbonate solution (800 ml.), dried and stripped of dichloromethane. The residue was triturated with hexane, affording (2α,5α,17β)-2-(diethoxymethyl)-17-[(tetrahydro-2H-pyran-2-yl)oxy]androstan-3-one (70.57 g., 49% yield, m.r. 165°–168° C.).

B. A solution of methanesulfonylhydrazide (3.33 g., 0.0303 mole) in tetrahydrofuran (70 ml., 30 ml. for rinsing) was added with stirring to a solution of (2α,5α,17β)-2-(diethoxymethyl)-17-[(tetrahydro-2H-pyran-2-yl)oxy]androstan-3-one (11.92 g., 0.025 mole) in tetrahydrofuran (190 ml.). The mixture was allowed to stand for 3 days at room temperature, heated under reflux for 4 hr. and stripped of volatiles. The residue was purified by crystallization and recrystallization from methanol, affording (5α,17β)-1′-(methylsulfonyl)-17-[(tetrahydro-2H-pyran-2-yl)oxy]-1′H-androstano[3,2-c]pyrazole (7.70 g., 65% yield, m.r. 168°–169° C.), the compound of Formula I wherein X and R$_{10}$ are CH$_3$, Y-Z is

R$_6$ and R$_{17\alpha}$ are H and R$_{17\beta}$ is

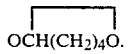

EXAMPLE 21

Dichloroacetic anhydride (4.60 g., 0.02 mole) was added with cooling to a solution of (17β)-4-methyl-1′-(methylsulfonyl)-1′H-androst-4-eno[3,2-c]pyrazol-17-ol (product of Example 13, 4.05 g., 0.0100 mole) in pyridine (25 ml.). The mixture was diluted with hydrochloric acid (2N, 200 ml.) and extracted with dichloromethane (100 ml.). The dichloromethane extract was washed with saturated aqueous sodium hydroxide solution (100 ml.), dried and stripped of volatiles. Crystallization of the residue from dichloroethane-methanol afforded (17β)-4-methyl-1′-(methylsulfonyl)-1′H-androst-4-eno[3,2-c]pyrazol-17-ol dichloroacetate (ester) (3.60 g., 70% yield, m.r. 207°–208° C.), the compound of Formula I wherein X and R$_{10}$ are CH$_3$, Y-Z is

R$_6$ and R$_{17\alpha}$ are H and R$_{17\beta}$ is OCOCHCl$_2$.

EXAMPLE 22

By the method of Example 21 (5α,17β)-1′-(methylsulfonyl)-1′H-androstano[3,2-c]pyrazol-17-ol (product of Example 12, 11.78 g., 0.0300 mole) was dichloroacetylated using dichloroacetic anhydride (14.39 g., 0.0600 mole plus 1 ml.) in pyridine. The reaction mixture was quenched in hydrochloric acid (2N, 1 l.). Recrystallization of the crude product (15.52 g., m.r. 167°–172° C.) from acetonitrile afforded (5α,17β)-1′-(methylsulfonyl)-1′H-androstano[3,2-c]pyrazol-17-ol dichloroacetate (ester) (10.85 g., 72% yield, m.r. 207°–208° C.), the compound of Formula I wherein X and R$_{10}$ are CH$_3$, Y-Z is

R$_6$ and R$_{17\alpha}$ are H and R$_{17\beta}$ is OCOCHCl$_2$.

EXAMPLE 23

By the method of part A of Example 1 (17α)-17-hydroxy-1′H-pregn-4-en-20-yno[3,2-c]pyrazole-4-carbonitrile (10.71 g., 0.0300 mole) was methanesulfonylated using methanesulfonyl chloride (4 ml., 5.92 g., 0.0516 mole) in pyridine (150 ml.). The product was purified by column chromatography on silica gel using dichloromethane-ether (99:1) as eluant followed by crystallization from methanol, affording (17α)-17-hydroxy-1′-(methylsulfonyl)-1′H-pregn-4-en-20- yno[3,2-c]pyrazole-4-carbonitrile (4.60 g., 35% yield, m.r. 238°–240° C.), the compound of Formula I wherein X and $R_{10}$ are $CH_3$, Y-Z is

$R_6$ is H, $R_{17\alpha}$ is C≡CH and $R_{17\beta}$ is OH.

EXAMPLE 24

A. By the method of part A of Example 20 (5α,17β)-17-hydroxyandrostan-3-one trifluoroacetate (ester) (0.344 mole) was diethoxymethylated using triethylorthoformate (126 ml.) and boron trifluoride etherate (140 ml.). The product was crystallized from methanol, affording (2α,5α,17β)-2-(diethoxymethyl)-17-hydroxyandrostan-3-one trifluoroacetate (ester) (118.7 g., 71% yield, m.r. 122°–123° C.).

B. By the method of part B of Example 20 (2α,5α,17β)-2-(diethoxymethyl)-17-hydroxyandrostan-3-one trifluoroacetate (ester) (48.86 g., 0.100 mole) was condensed with methansulfonylhydrazide (13.32 g., 0.121 mole). The product was crystallized from methanol (41.64 g., 87% yield, m.r. 195°–198° C.). Part (12.0 g.) of the crystallized product was recrystallized from dichloromethane-methanol, affording (5α,17β)-1′-(methyl-sulfonyl)-1′H-androstano[3,2-c]pyrazol-17-ol trifluoroacetate (ester) (11.44 g., m.r. 192°–195° C.), the compound of Formula I wherein X and $R_{10}$ are $CH_3$, Y-Z is

$R_6$ and $R_{17\alpha}$ are H and $R_{17\beta}$ is $OCOCF_3$.

EXAMPLE 25

A. By the method of part A of Example 20 (5α,17β)-17-methoxyandrostan-3-one (45.67 g., 0.15 mole) was diethoxymethylated using triethylorthoformate (55.0 ml., 49.0 g., 0.33 mole) and boron trifluoride etherate (50.0 ml., 57.7 g., 0.407 mole), affording (2α,5α,17β)-2-(diethoxymethyl)-17-methoxyandrostan-3-one (71.81 g.).

B. By the method of part B of Example 20 (2α,5α,17β)-(diethoxymethyl)-2-(diethoxymethyl)-17-methoxyandrostan-3-one (61.81 g., assumed to be 0.129 mole) was condensed with methanesulfonylhydrazide (16.5 g., 0.15 mole). The product was crystallized from methanol, affording (5α,17β)-17-methoxy-1′-(methylsulfonyl)-1′H-androstano[3,2-c]pyrazole (42.62 g., 70% yield), the compound of Formula I wherein X and $R_6$ are $CH_3$, Y-Z is

$R_6$ and $R_{17\alpha}$ are H and $R_{17\beta}$ is $OCH_3$.

EXAMPLE 26

A. A suspension of (5α,17α)-17-hydroxypregn-20-yn-3-one (62.9 g., 0.200 mole) in acetic anhydride (480 ml.), dimethylsulfoxide (480 ml.) and acetic acid (100 ml.) was stirred for 5 days at room temperature. Volatiles were removed under vaccum, using first a water pump and then a mechanical pump. Recrystallization of the residue from acetonitrile afforded (5α,17α)-17-[(methylthio)methoxy]pregn-20-yn-3-one (60.40 g., 81% yield, m.r. 142°–144° C.).

B. By the method of part A of Example 20 (5α,17α)-17[(methylthio)methoxy]pregn-20-yn-3-one (56.19 g., 0.15 mole) was diethoxymethylated using triethylorthoformate (55.0 ml., 49.0 g., 0.33 mole) and boron trifluoride etherate (50.0 ml., 57.7 g., 0.407 mole), affording (2α,5α,17α)-2-(diethoxymethyl)-17-[(methylthio)methoxy]pregn-20-yn-3-one as an oil.

C. By the method of part B of Example 20 (2α,5α,17α)-2-(diethoxymethyl)-17-[(methylthio)methoxy]-pregn-20-yn-3-one (the entire product of part B of this example) was condensed with methanesulfonylhydrazide (18.15 g., 0.165 mole). The product was crystallized from methanol, affording (5α,17α)-1′-(methylsulfonyl)-17-[(methylthio)methoxy]-1′H-pregn-20-yno[3,2-c]pyrazole (50.75 g., 71% yield for the two steps, m.r. 149°–151° C.), the compound of Formula I wherein X and $R_{10}$ are $CH_3$, Y-Z is

$R_6$ is H, $R_{17\alpha}$ is C≡CH and $R_{17\beta}$ is $OCH_2SCH_3$.

EXAMPLE 27 m-Chloroperbenzoic acid (assumed to be 80% pure, 11.86 g., 0.055 mole) was added with stirring to a solution of (5α,17α)-1′-(methylsulfonyl)-17-[(methylthio)methoxy]-pregn-20-yno[3,2-c]pyrazole (11.92 g., 0.0250 mole) in dichloromethane (200 ml.) maintained at 0° C. Stirring was continued for 4 hr. at 0° C., the mixture was filtered, and the residue was crystallized from dichloromethane-methanol, affording (5α,17α)-1′-(methylsulfonyl)-17-[(methylsulfonyl)methoxy]-1′H-pregn-20-yno[3,2-c]pyrazole (11.57 g., 91% yield, m.r. 223°–225° C.), the compound of Formula I wherein X and $R_{10}$ are $CH_3$, Y-Z is

$R_6$ is H, $R_{17\alpha}$ is C≡CH and $R_{17\beta}$ is $OCH_2SO_2CH_3$.

EXAMPLE 28

A. A mixture of (5α,17α)-17-hydroxypregn-20-yn-3-one (62.89 g., 0.200 mole) in trifluoroacetic anhydride (100 ml.) and dichloromethane (800 ml.) was stirred for 16 hr. at room temperature, then stripped of volatiles under vacuum. A solution of the residue in dichloromethane (300 ml.) was washed with half-saturated aqueous sodium bicarbonate solution, dried and stripped of dichloromethane. Recrystallization of the residue from cyclohexane afforded (5α,17α)-17-[(trifluoroacetyl)oxy]pregn-20-yn-3-one (66.01 g., 80% yield, m.r. 173°–175° C.).

B. By the method of part A of Example 20 (5α,17α)-17-[(trifluoroacetyl)oxy]pregn-20-yn-3-one (61.55 g., 0.150 mole) was diethoxymethylated using triethylorthoformate (55.0 ml., 49.0 g., 0.33 mole) and boron trifluoride etherate (50 ml., 57.7 g., 0.407 mole). The crude product was re-diethoxymethylated using the same amounts of reagents because it showed unchanged starting material by TLC. Part (16.59 g.) of the product was purified by crystallization from hexane and was recrystallized from hexane, affording (2α,5α,17α)-2-(diethoxymethyl)-17-[(trifluoroacetyl)oxy]pregn-20-yn-3-one (m.r. 134.5°–135.5° C.).

C. By the method of part B of Example 20 (2α,5α,17α)-2-(diethoxymethyl)-17-[(trifluororacetyl)oxy]-pregn-20-yn-3-one (the entire product of a rerun of part B of this example) was condensed with methanesulfonylhydrazide (18.15 g., 0.165 mole). The product was crystallized from methanol (200 ml.) - water (25 ml.), affording (5α,17α)-1'-(methylsulfonyl)-1'H-pregn-20-yno[3,2-c]pyrazol-17-ol trifluoroacetate (ester) (53.08 g., 69% yield for the two steps, m.r. 166°–168° C.), the compound of Formula I wherein X and $R_{10}$ are $CH_3$, Y-Z is

$R_6$ is H, $R_{17\alpha}$ is C≡CH and $R_{17\beta}$ is $OCOCF_3$.

EXAMPLE 29

By the method of part A of Example 1 (5α,17β)-17-methyl-1'H-androstano[3,2-c]pyrazol-17-ol (32.8 g., 0.100 mole) was ethanesulfonylated using ethanesulfonyl chloride (13 g., 0.10 mole) in pyridine (250 ml.). The product was purified by fractional crystallizaton from acetonitrile, affording (5α,17β)-1'-(ethylsulfonyl)-17-methyl-1'H-androstano[3,2-c]pyrazol-17-ol (9.8 g., 23% yield, m.r. 197°–199° C.), the compound of Formula I wherein X is $CH_3CH_2$, Y-Z is

$R_6$ is H, $R_{10}$ and $R_{17\alpha}$ are $CH_3$ and $R_{17\beta}$ is OH.

EXAMPLE 30

Silver nitrate (0.50 g.) and N-bromosuccinimide (5.40 g., 0.30 mole) were added with stirring at room temperature to a solution of (5α,17α)-1'-(methylsulfonyl)-1'H-pregn-20-yno[3,2-c]pyrazol-17-ol (10.91 g., 0.0262 mole) in acetone (200 ml.). Stirring was continued for 75 minutes. The mixture was diluted with ice-water (500 ml.) and extracted twice with dichloromethane (200 ml., 100 ml.). The combined dichloromethane extracts were washed with water (300 ml.), dried and stripped of solvent. Crystallization of the residue from methanol (50 ml.) afforded (5α,17α)-21-bromo-1'-(methylsulfonyl)-1'H-pregn-20-yno[3,2-c]pyrazol-17-ol (9.15 g., 71% yield, m.r. 205°–208° C.), the compound of Formula I wherein X and $R_{10}$ are $CH_3$, Y-Z is

$R_6$ is H, $R_{17\alpha}$ is C≡CBr and $R_{17\beta}$ is OH.

EXAMPLE 31 m-Chloroperbenzoic acid (assumed to be 80% pure, 5.39 g., 0.025 mole) was added with stirring and ice bath cooling to a solution of (5α,17α)-1'-(methylsulfonyl)-17-[(methylthio)methoxy]pregn-20-yno[3,2-c]pyrazole (11.9 g., 0.025 mole) in dichloromethane (200 ml.). Stirring was continued and unreacted starting material was shown by TLC to be present after one day. More m-chloroperbenzoic acid (0.50 g.) was added and stirring was continued for 1 hr. Unreacted starting material was still present as shown by TLC, so still more m-chloroperbenzoic acid (0.50 g.) was added with stirring. The next test for starting material was negative. The reaction mixture was washed with saturated aqueous sodium bicarbonate solution, dried over magnesium sulfate, and stripped of dichloromethane. Two crystallizations of the residue from ethyl acetate gave a product (7.00 g.) having m.r. 198°–203° C., which was further purified by column chromatography on silica gel (Kieselgel 60, 200 g.) using dichloromethane-ether (9:1) as eluant. Fractions of 400 ml. were taken. Recrystallization of the combined residues of fractions 5–9 from ethyl acetate afforded (5α,17α)-1'-(methylsulfonyl)-17-[(methylsulfinyl)methoxy]-1'H-pregn20-yno[3,2-c]pyrazole (4.18 g., 34% yield, m.r. 200°–203° C.), the compound of Formula I wherein X and $R_{10}$ are $CH_3$, Y-Z is

$R_6$ is H, $R_{17\alpha}$ is C≡CH and $R_{17\beta}$ is $OCH_2SOCH_3$.

EXAMPLE 32

This is a further example of the third process aspect of the invention, which is also exemplified in part D of Example 1, and the preparation of (5α,17α)-1'-(methylsulfonyl)-1'H-pregn-20-yno[3,2-c]pyrazol-17-ol, which is also exemplified in parts A-D of Example 1.

A. Benzoyl chloride (33.9 ml., 0.29 mole) was added dropwise with stirring during 30 min. at room temperature to a slurry of (5α,17α)-17-hydroxy-2-(hydroxymethylene)pregn-20-yn-3-one (100 g., 0.29 mole) and potassium carbonate (40.4 g., 0.29 mole) in acetone (700 ml.). Stirring was continued at room temperature for 18 hr. The mixture was filtered, the filtercake was washed with acetone (100 ml.), and the filtrate was stripped of volatiles under vacuum. Crystallization of the residue from toluene (750 ml.) with charcoal decolorization afforded (5α,17α)-2-[(benzoyloxy)methylene]-17-hydroxypregn-20-yn-3-one in two crops (81.7 g., 98.4% pure by HPLC; 11.9 g., 98.6% pure by HPLC; 72% yield). Recrystallization of part (15 g.) of the combined crops from acetone (150 ml.) gave product (11.4 g.) having m.r. 214°–215° C.

B. A solution of methanesulfonylhydrazide (1.9 g., 0.0168 mole) and methanesulfonic acid (98%, 0.074 ml., 0.00112 mole) in acetic acid (6.5 ml.) was added with stirring during 30 sec. to a solution of (5α,17α)-2-[(benzoyloxy)methylene]-17-hydroxypregn-20-yn-3-one (5 g., 0.0112 mole) in dichloromethane (25 ml.) and acetic acid (6.5 ml.) held at 0° C. The resulting mixture was allowed to stand at 4° C. for 18 hr. Dichloromethane (100 ml.) and water (100 ml.) were added. The dichloromethane layer was separated, washed with saturated aqueous sodium bicarbonate solution (100 ml.), dried over magnesium sulfate, filtered and stripped of volatiles. The residue (5.3 g.) was shown by HPLC to consist of (5α,17α)-1'-(methylsulfonyl)-1'H-pregn-20-yno[3,2-c]pyrazol-17-ol (95.2%) and an impurity identified as the 4',5'-addition product thereof with methanesulfonylhydrazide (2.3%).

ANTIANDROGENIC PROPERTIES OF THE COMPOUNDS

Utility of the compounds of Formula I as antiandrogenic agents was evaluated in two tests, the in vitro rat prostate androgen receptor competition assay and the in vivo test for antiandrogenic activity in the castrated immature male rat.

In the rat prostate androgen receptor competition assay prostate glands from 24-hr. castrated adult male rats weighing approximately 250 g. were homogenized in aqueous pH 7.4 buffer containing triaziquone (10 mM), sodium molybdate (20mM), 1,4-dithiothreitol (2.0 mM) and glycerol (10%). The homogenate was centrifuged at the equivalent of 105,000 g. for 1 hr. Aliquots of the supernatant liquid (cytosol) were incubated with methyltrienolone labelled with tritium in the 17α-methyl (5 nM final concentration) in either the absence or presence of increasing concentrations ($10^{-9}$–$10^{-5}$ M) of unlabelled methyltrienolone as a reference or a test compound for 1 hr. or overnight (approximately 18 hr.) at 4° C. Triamcinolone acetonide (1 μM) was added to the cytosol before incubation to block the low affinity binding of labelled methyltrienolone to progesterone and glucocorticoid receptors. After the 1 hr. or 18 hr. incubation period an aqueous suspension of dextran (T-70, 0.05%) - coated charcoal (1%) was added to the incubation mixture and incubation was continued for 5 min. The incubation mixture was centrifuged to remove charcoal (nonprotein)-bound labelled methyltrienolone. The supernatant was separated and its radioactivity was counted to determine the concentration of protein-bound labelled methyltrienolone. The relative binding affinity was calculated as the concentration of test compound required to reduce the concentration of protein-bound labelled methyltrienolone by 50% as a percentage relative to unlabelled methyltrienolone. Androgens including the naturally occurring testosterone and 5α-dihydrotestosterone (stanolone) and the synthetic methyltrienolone and stanozolol (a steroido[3,2-c]pyrazole of above-cited U.S. Pat. No. 3,704,295) show high relative binding affinities and 1 hr./18 hr. relative binding affinity ratios close to unity. In general antiandrogens including flutamide and cyproterone acetate show lower relative binding affinities and 1 hr./18 hr. relative binding affinity ratios greater than 10.

In the test for antiandrogenic activity in the castrated immature male rat weanling male rats were castrated and, beginning one week later, grouped by body weight and medicated orally with an ethanol (10%)—cottonseed oil suspension of test compound and testosterone propionate (0.8 mg./kg.) for 10 consecutive days. On the day following the last medication the rats were weighed and killed. The ventral prostate gland, seminal vesicles and levator ani muscle of each rat were removed, blotted and weighed. Antiandrogenic potency is defined as the $AED_{50}$, which is the approximate dose of test compound required to inhibit testosterone propionate stimulated prostate weight gain by 50%. Test compounds which did not inhibit prostate weight gain by 50% but nevertheless showed significant ($P<0.01$) inhibition at a dose of 100 mg./kg. are considered active and are assigned an $AED_{50}$ value of >100.

The following results were obtained.

| Compound of Example | Relative Binding Affinity 1 Hr. | Relative Binding Affinity 18 Hr. | Antiandrogenic Potency $AED_{50}$ (mg./kg. orally) |
|---|---|---|---|
| 1 | 2.1 | 0.09 | 14 |
| 2 | 12.1 | 0.9 | 16 |
| 3 | 0.4 | <0.01 | >100 |
| 4 | 16.1 | 0.9 | 10 |
| 5 | 1.5 | 0.03 | 100 |
| 6 | 2.6 | 0.12 | <<100 |
| 7 | 2.8 | 0.1 | 41 |
| 8 | 0.6 | 0.01 | <100 |
| 9 | 3.6 | 0.08 | 33 |
| 10 | 17.8 | 1.4 | 3 |
| 11 | 0.83 | <0.01 | 100 |
| 12 | 25.8 | 2.34 | >100 |
| 13 | 18.9 | 2.1 | Active at 11 (flat dose-response) |
| 14 | 0.07 | <0.01 | >100 |
| 15 | 9.8 | 0.7 | >>100 |
| 16 | 7.0 | 0.05 | 14 |
| 17 | 9.3 | 0.9 | 24 |
| 18 | 1.0 | 0.05 | 38 |
| 19 | 5.1 | 0.33 | >100 |
| 20 | <0.01 | <0.01 | 100 |
| 21 | 6.4 | 0.56 | >>100 |
| 22 | 9.0 | 0.45 | >100 |
| 23 | 0.2 | <0.01 | >100 |
| 24 | 8.27 | 0.90 | 100 |
| 25 | <0.01 | <0.01 | 100 |
| 26 | <0.01 | <0.01 | 24 |
| 27 | 0.059 | <0.01 | >100 |
| 28 | 0.37 | <0.01 | 10 |
| 29 | 2.5 | 0.24 | <100 |
| 30 | 0.09 | <0.01 | 100 |
| 31 | 0.22 | <0.01 | 10 |

In carrying out the fourth process aspect of the invention the antiandrogenically effective amount of the compound of Formula I can be estimated from the foregoing test results. This aspect of the invention is preferably carried out using a compound of Formula I in accordance with the preferred composition of matter aspect of the invention, most preferably with the compound of Example 1 or the compound of Example 16 and is contemplated to be carried out in the human male in the treatment of benign prostatic hypertrophy or in the human female in the treatment of polycystic ovarian disease or both or in other human disease or metabolic disorder amenable to treatment with an antiandrogenic agent. It can be carried out using the compound of Formula I alone, but is preferably carried out using a composition in accordance with the second composition of matter aspect of the invention.

The Compositions

The compositions in accordance with the second composition of matter aspect of the invention can be prepared for oral, parenteral, rectal or vaginal administration and can be in solid or liquid dosage form including capsules, tablets, suppositories, solutions, suspensions and emulsions. Conventional pharmaceutically acceptable vehicles and techniques are used in preparing these dosage forms.

We claim:

1. A compound having the structural formula

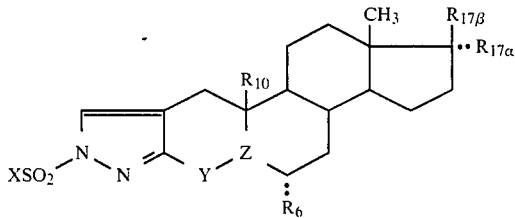

wherein
X is CH₃, CH₃CH₂, CH₃CH₂CH₂ or ClCh₂;
Y-Z is

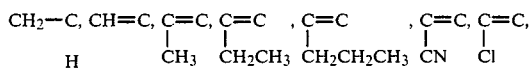

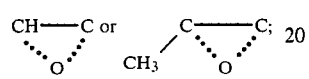

R₆ is H or CH₃ when Y-Z is CH=C or H when Y-Z is other than CH=C;
R₁₀ is H or CH₃;
R₁₇α taken alone is H, C₃, CH₂CH₃, CH=CH₂, C≡CH or C≡CBr;
R₁₇β taken alone is OH, OCOCHCl₂, OCOCF₃, OCH₃, OCH₂SCH₃,
OCH₂SOCH₃, OCH₂SO₂CH₃ or

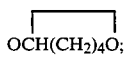

and
R₁₇α taken together with R₁₇β is OCh₂CH₂O.
2. A compound according to claim 1 wherein X is CH₃ Y-Z is

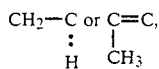

R₆ is H, R₁₀ is CH₃, R₁₇α is CH₃ or C≡CH and R₁₇β is OH.

3. (5α,17α)-1'-(Methylsulfonyl)-1'H-pregn-20-yno[3,2-c]pyrazol-17-ol according to claim 2.

4. (5α,17β)-17-Methyl-1'-(methylsulfonyl)-1'H-androstano[3,2-c]pyrazol-17-ol according to claim 2.

5. (17β)-4,17-Dimethyl-1'-(methylsulfonyl)-1'H-androst-4-eno[3,2-c]pyrazol-17-ol according to claim 2.

6. (17α)-4-Methyl-1'-(methylsulfonyl)-1H-pregn-4-en-20-yno[3,2-c]pyrazol-17-ol according to claim 2.

7. The process of preparing a compound according to claim 1 which comprises sulfonylating the corresponding compound having the structural formula

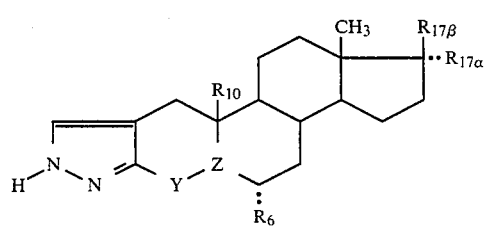

with the corresponding compound having the structural formula

XSO₂Q wherein Q is Cl, Br or OSO₂X.

8. The process according to claim 7 wherein X is CH₃, Y-Z is

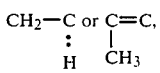

R₆ is H, R₁₀ is CH₃, R₁₇α is CH₃ or CH≡CH and R₁₇β is OH.

9. The process of preparing a compound according to claim 1 which comprises condensing the corresponding compound having the structural formula

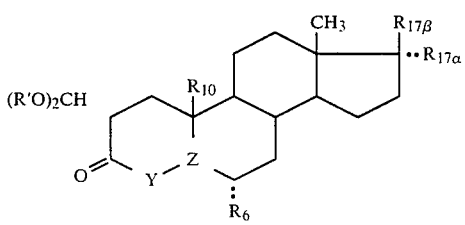

with the corresponding compound having the structural formula

XSO₂NHNH₂ wherein R' is CH₃ or CH₃CH₂.

10. The process according to claim 9 wherein X is CH₃, Y-Z is

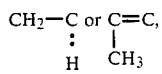

R₆ is H, R₁₀ is CH₃, R₁₇α is CH₃ or C≡CH and R₁₇β is OH.

11. The process according to claim 10 wherein R' is CH₃CH₂.

12. The process of preparing a compound according to claim 1 which comprises condensing the corresponding compound having the structural formula

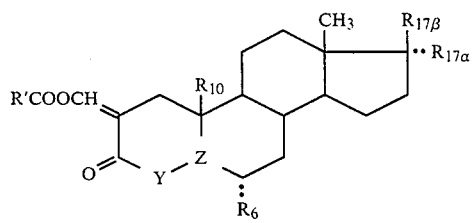

with the corresponding compound having the structural formula

XSO₂NHNH₂ wherein R' is CH₃, CH₃CH₂ or C₆H₅.

13. The process according to claim 12 wherein X is CH₃, Y-Z is

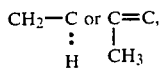

$R_6$ is H, $R_{10}$ is $CH_3$, $R_{17\alpha}$ is $CH_3$ or $C\equiv CH$ and $R_{17\beta}$ is OH.

14. The process according to claim 13 wherein Y-Z is

$R_{17\alpha}$ is $C\equiv CH$ and R' is $C_6H_5$.

15. The process for effecting an antiandrogenic response in a mammal which comprises administering to the mammal an antiandrogenically effective amount of a compound according to claim 1.

16. The process according to claim 15 wherein X is $CH_3$, Y-Z is

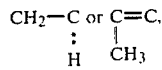

$R_6$ is H, $R_{10}$ is $CH_3$, $R_{17\alpha}$ is $CH_3$ or $C\equiv CH$ and $R_{17\beta}$ is OH.

17. A composition which comprises an antiandrogenically effective concentration of a compound according to claim 1 and a pharmaceutically acceptable vehicle.

18. A composition according to claim 17 wherein X is $CH_3$, Y-Z is

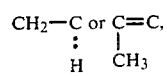

$R_6$ is H, $R_{10}$ is $CH_3$, $R_{17\alpha}$ is $CH_3$ or $C\equiv CH$ and $R_{17\beta}$ is OH.

19. 4-Methyl-1'-(methylsulfonyl)-1'H-androst-4-eno[3,2-c]pyrazol-17-one.

* * * * *

UNITED STATES PATENT AND TRADEMARK OFFICE
CERTIFICATE OF CORRECTION

PATENT NO. : 4,684,636

DATED : August 4, 1987

INVENTOR(S) : Robert G. Christiansen et al.

It is certified that error appears in the above-identified patent and that said Letters Patent is hereby corrected as shown below:

Item [56], Covering page, line 6, "Bahcock" should read --Babcock--.

Item [56], Covering page, line 9, "Dupont Paul E." should read --Paul E. Dupont--.

In the title of invention:

Covering page and column 1, line 5,
"PROCESSES FOR PREPARATION METHOD OF USE" should read
--PROCESSES FOR PREPARATION, METHOD OF USE--.

Column 2, line 30, "$OCH_2SOCH$" should read --$OCH_2SOCH_3$--.

Column 3, line 15, Formula IV,

Column 6, line 29, "yno[3,2-c]pyrazol-7-ol" should read --yno[3,2-c]pyrazol-17-ol--.

UNITED STATES PATENT AND TRADEMARK OFFICE
CERTIFICATE OF CORRECTION

PATENT NO. : 4,684,636
DATED : August 4, 1987
INVENTOR(S) : Robert G. Christiansen et al.

It is certified that error appears in the above-identified patent and that said Letters Patent is hereby corrected as shown below:

Column 6, line 58, "affording (5α, 17α -1'-(meth" should read
--affording (5α, 17α)-1'-(meth--.

Column 7, line 43, "(methylsulfonyl)-1'-H-pregn" should read
--(methylsulfonyl)-1'H-pregn--.

Column 7, line 47, "Example 1 (17β)-1'" should read
--Example 1 (17β)-1'--.

Column 8, line 11 "0.113 5 mole)" should read
--0.113 mole)--.

Column 8, line 29, "Example 1 (17α-1'H" should read
--Example 1 (17α)-1'H--.

Column 8, line 39, "X is $CH_3CH_2$" should read
--X is $CH_3CH_2$, Y-Z is--.

Column 10, line 23, "Y-Z" should read -- Y-Z is --.

UNITED STATES PATENT AND TRADEMARK OFFICE
CERTIFICATE OF CORRECTION

PATENT NO. : 4,684,636

DATED : August 4, 1987

INVENTOR(S) : Robert G. Christiansen et al.

It is certified that error appears in the above-identified patent and that said Letters Patent is hereby corrected as shown below:

Column 10, line 51, "H and $R_{17}62$ is OH" should read --H and $R_{17\beta}$ is OH--.

Column 11, line 7, "$R_6$ and $R_{17\alpha}$ is OH" should read -- $R_6$ and $R_{17\alpha}$ are H and $R_{17\beta}$ is OH --

Column 12, line 45, "$R_6$ is H, $R_{17\alpha}$ (is C≡CH and R)$_{17\beta}$ is OH" should read --$R_6$ is H, $R_{17\alpha}$ is C≡CH and $R_{17\beta}$ is OH--.

Column 13, line 16, "$R_{17\alpha}$ (is C≡CH and R)$_{17\beta}$ is OH" should read --$R_{17\alpha}$ is C≡CH and $R_{17\beta}$ is OH--.

Column 14, line 27, "dichloroethane-methanol" should read --dichloromethane-methanol--.

Column 15, line 46, "(2α,5α,17β)-(diethoxymethyl)-2-(diethoxymethyl)-17-methoxy-androstan-3-one" should read --(2α,5α,17β)-2-(diethoxymethyl)-17-methoxyandrostan-3-one--.

UNITED STATES PATENT AND TRADEMARK OFFICE
CERTIFICATE OF CORRECTION

PATENT NO. : 4,684,636

DATED : August 4, 1987

INVENTOR(S) : Robert G. Christiansen et al.

It is certified that error appears in the above-identified patent and that said Letters Patent is hereby corrected as shown below:

Column 17, line 7, claim 1, "17-[(trifluororacetyl)oxy]" should read --17-[(trifluoroacetyl)oxy]--

Column 21, line 12, claim 1, "or ClCh$_2$" should read --or ClCH$_2$--.

Column 21, line 16, claim 1, "CH$_2$-C" should read --CH$_2$-C--.
$\phantom{--CH_2-}$H $\qquad\qquad\qquad\qquad$ H Column 21, line 26, claim 1, "R$_{17\alpha}$ taken alone is H, C$_3$, CH$_2$CH$_3$, CH=CH$_2$" should read --R$_{17\alpha}$ taken alone is H, CH$_3$, CH$_2$CH$_3$, CH=CH$_2$--.

Column 21, line 37, claim 1, "R$_{17\beta}$ is OCh$_2$CH$_2$O" should read --R$_{17\beta}$ is OCH$_2$CH$_2$O--.

Column 21, line 40, claim 2, "CH$_3$ Y-Z is" should read --CH$_3$, Y-Z is--.

UNITED STATES PATENT AND TRADEMARK OFFICE
CERTIFICATE OF CORRECTION

PATENT NO. : 4,684,636

DATED : August 4, 1987

INVENTOR(S) : Robert G. Christiansen et al.

Page 5 of 5

It is certified that error appears in the above-identified patent and that said Letters Patent is hereby corrected as shown below:

Column 22, line 25, claim 9,

"$(R'O)_2CH$" should read --$(R'O)_2CH$--.

Signed and Sealed this

Twenty-sixth Day of April, 1988

Attest:

DONALD J. QUIGG

*Attesting Officer*  *Commissioner of Patents and Trademarks*